United States Patent [19]

Young

[11] Patent Number: 5,605,456
[45] Date of Patent: Feb. 25, 1997

[54] DENTAL ARTICULATOR

[76] Inventor: Richard Young, 313 E. Stroop Rd., Kettering, Ohio 45429

[21] Appl. No.: 511,530

[22] Filed: Aug. 4, 1995

[51] Int. Cl.$^6$ .................................................. A61C 11/00
[52] U.S. Cl. ................................. 433/60; 433/54; 433/58
[58] Field of Search ................................. 433/54, 57, 58, 433/60, 66

[56] References Cited

U.S. PATENT DOCUMENTS

| 613,772 | 11/1898 | Moffitt | 433/57 |
|---|---|---|---|
| 1,096,195 | 5/1914 | Roberts | 433/60 |
| 1,322,386 | 11/1919 | Wilson . | |
| 1,736,006 | 11/1929 | Hagman . | |
| 2,119,896 | 6/1938 | Van Dorn et al. | 32/32 |
| 2,621,407 | 12/1952 | Schlesinger | 32/32 |
| 3,772,788 | 11/1973 | Gerber | 433/58 X |
| 3,815,242 | 6/1974 | Martfay et al. | 32/32 |
| 4,219,329 | 8/1980 | Celanza | 433/58 |
| 4,744,751 | 5/1988 | Finkelstein et al. | 433/60 |
| 5,221,203 | 6/1993 | Callne | 433/58 |

FOREIGN PATENT DOCUMENTS

| 180074 | 8/1905 | Germany | 433/54 |
|---|---|---|---|

Primary Examiner—Nicholas D. Lucchesi
Attorney, Agent, or Firm—Biebel & French

[57] ABSTRACT

A dental articulator comprises a maxillary clamp, a clamp support, a mandibular clamp and a mandibular clamp detent. The clamp support includes a first post defining a first set of engagement sites, a second post defining a second set of engagement sites, and a hinge pivotally supposing the maxillary clamp. The mandibular clamp detent engages with corresponding engagement sites of the first and second sets of engagement sites to position the mandibular clamp relative to the maxillary clamp. In preferred form, the mandibular and maxillary clamps each include a collet for embracing a first dental model and a cam threadedly engaging the collet for tightening the collet around such a dental model. In an especially preferred form, the collet includes a flexible band defining periodic apertures along a length of the band and the cam defines a thread engaging a potion of the periodic apertures to loosen or tighten the collet. In another especially preferred embodiment of the dental articulator, the engagement sites on the clamp support are defined by sockets on facing sides of the first and second posts. The mandibular clamp detent includes a sleeve coupled to the mandibular clamp, a spring positioned in the sleeve, a pair of threaded pins relatively biased by the spring and projecting out of the sleeve in different directions for engagement with corresponding sockets on the posts, and a pair of nuts each threadedly engaged with one of the pins for abutment against the sleeve.

10 Claims, 4 Drawing Sheets

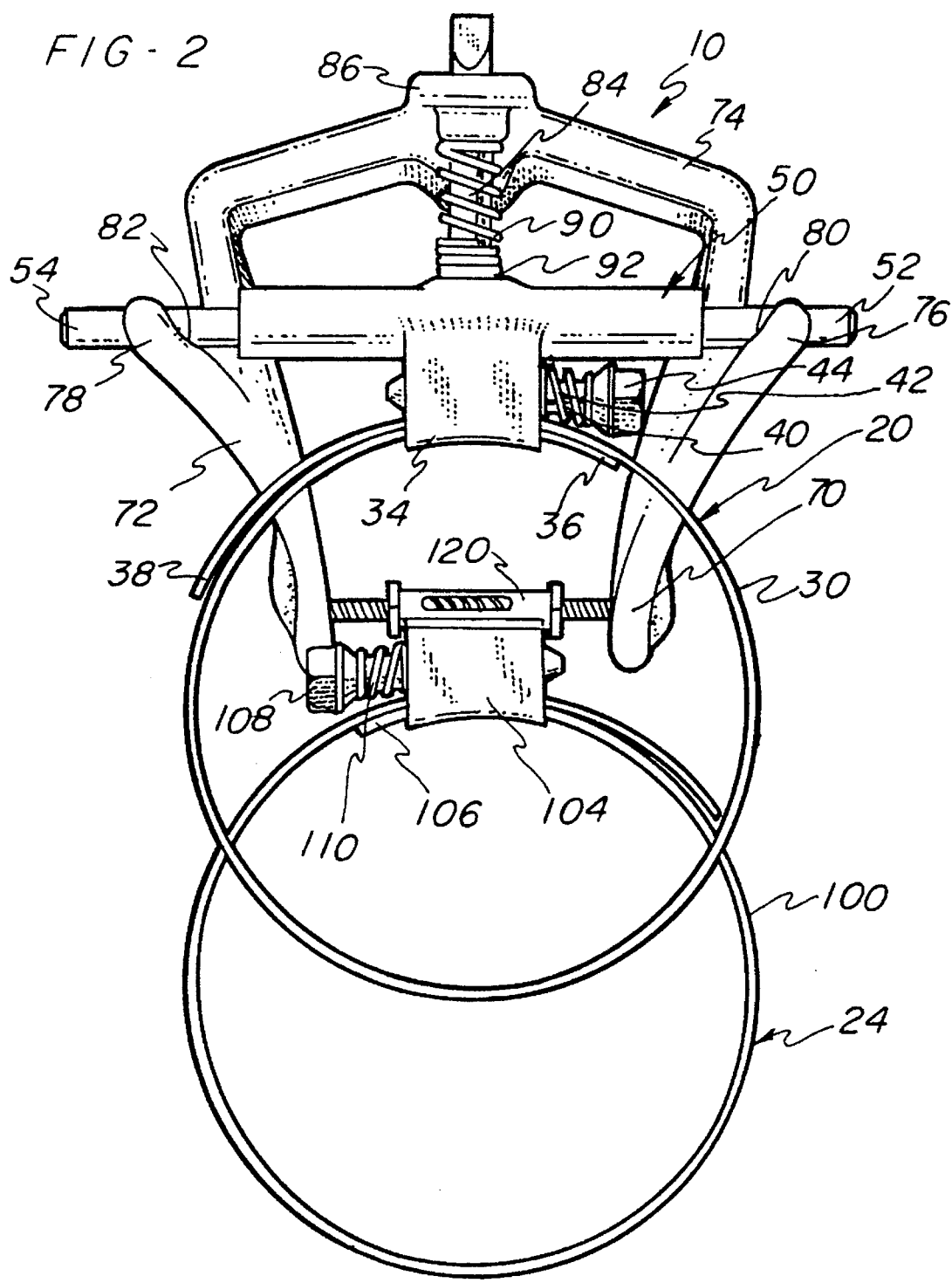

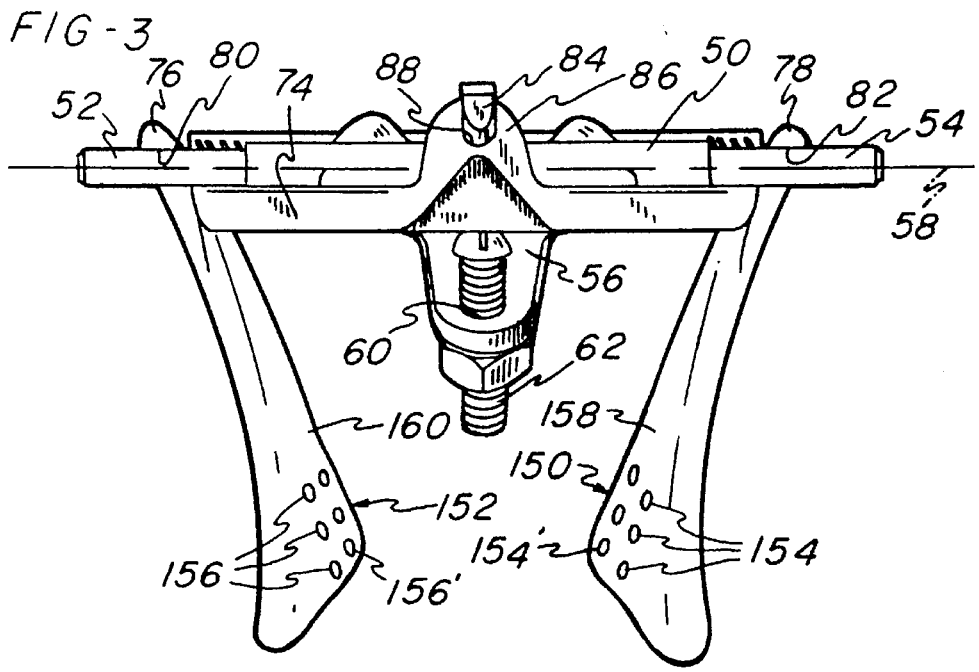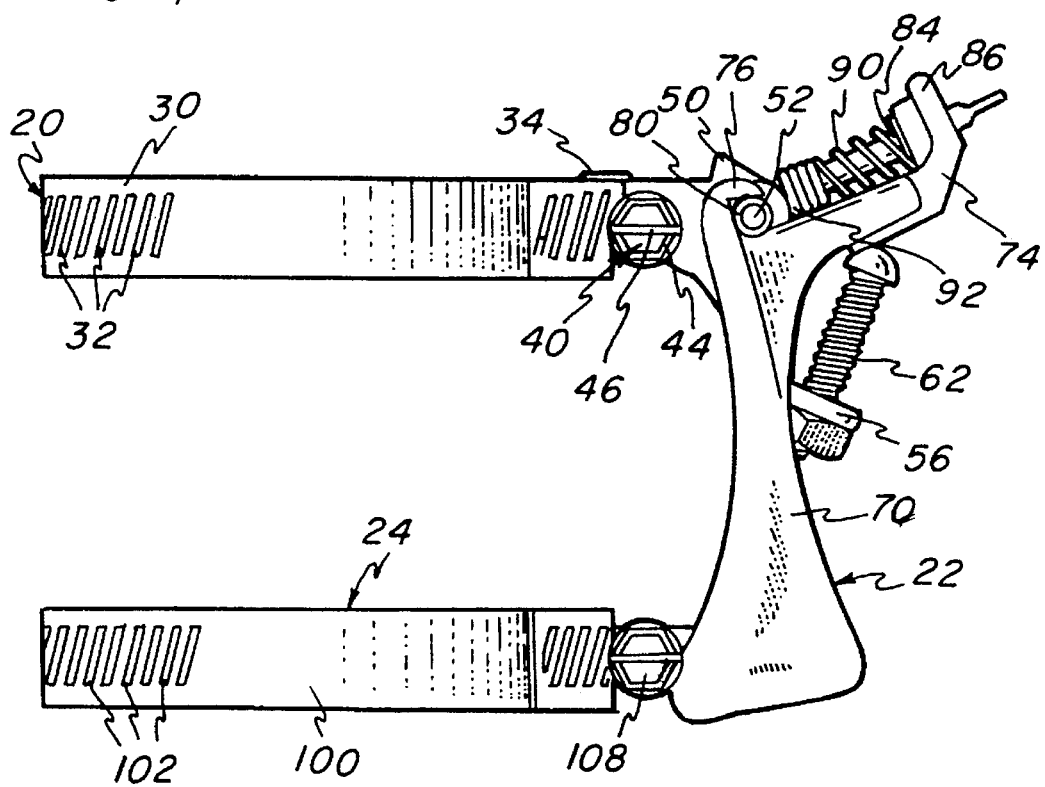

DENTAL ARTICULATOR

BACKGROUND OF THE INVENTION

1. Field of the Invention

This invention relates generally to the field of dental apparatus, and more particularly relates to a dental articulator which is relatively simple to manufacture and use.

2. Description of the Related Art

A dental articulator positions dental models such as castings of upper and lower jaws of a patient to permit a dentist to fabricate a dental prosthesis such as a denture outside the patient's mouth. In order to permit the dentist to fabricate a comfortable prosthesis, the geometry of the patient's mouth must be reproduced with a high degree of accuracy. Among the degrees of freedom which must be reproduced are the vertical bite, any lateral or protrusive misalignments of the maxilla (upper jaw) and mandible (lower jaw), and the inclinations of the maxilla and mandible relative to an axis passing through the condyles when the mouth is closed.

On the other hand, the articulator must be inexpensive to manufacture and simple to use so that the prosthesis may be produced efficiently. One technique for securing dental castings to articulators is to adhere the castings to plates using plaster of paris or the like. Not only is this technique expensive, time consuming and dirty, but it is difficult to remove and then accurately reinstall the castings on the plates if the dentist must interrupt work on one prosthesis to work on another. Various clamping systems have been proposed for mounting dental castings in articulators, but these have tended to be complicated and expensive. There remains a need in the art for a dental articulator which permits dental models to be quickly, easily and accurately installed, removed and, if necessary, reinstalled.

SUMMARY OF THE INVENTION

This need is addressed by a dental articulator comprising a maxillary clamp, a clamp support, a mandibular clamp and a mandibular clamp detent. The clamp support includes a first post defining a first set of engagement sites, a second post defining a second set of engagement sites, and a hinge pivotally supporting the maxillary clamp. The mandibular clamp detent engages with corresponding engagement sites of the first and second sets of engagement sites to position the mandibular clamp relative to the maxillary clamp.

In preferred form, the mandibular and maxillary clamps each include a collet for embracing a first dental model and a cam threadedly engaging the collet for tightening the collet around the model. In an especially preferred form, the collet includes a flexible band defining periodic apertures along a length of the band and the cam defines a thread engaging a portion of the periodic apertures to loosen or tighten the collet.

In another especially preferred embodiment of the dental articulator, the engagement sites on the clamp support are defined by sockets on facing sides of the first and second posts. The mandibular clamp detent includes a sleeve coupled to the mandibular clamp, a spring positioned in the sleeve, a pair of threaded pins relatively biased by the spring and projecting out of the sleeve in different directions for engagement with corresponding sockets on the posts, and a pair of nuts each threadedly engaged with one of the pins for abutment against the sleeve.

In use, maxillary and mandibular dental models are secured in the maxillary and mandibular clamps, respectively. The installation and removal of the models is particularly fast and simple where the maxillary and mandibular clamps include collets tightened or loosened by cams to secure or release the models. By selecting an appropriate pair of corresponding engagement sites on the first and second posts of the clamp support, the mandibular clamp is positioned relative to the maxillary clamp such that the vertical bite and the protrusive misalignment of the patient's teeth are reproduced in the relative positions of the maxillary and mandibular models.

Accordingly, it is one object of the invention to provide a dental articulator which permits dental models to be quickly, easily and accurately installed, removed and, if necessary, reinstalled. This and other objects, features and advantages of the present invention will be described in further detail in connection with the preferred embodiments of the invention shown in the accompanying drawings.

BRIEF DESCRIPTION OF THE DRAWINGS

FIG. 2 is a top plan view of the dental articulator of FIG. 1;

FIG. 3 is a rear elevational of a mandibular clamp and a clamp support for the dental articulator of FIG. 2;

FIG. 4 is a side elevational view of the clamp support of FIG. 1;

DETAILED DESCRIPTION OF THE PREFERRED EMBODIMENT

Figure 1:
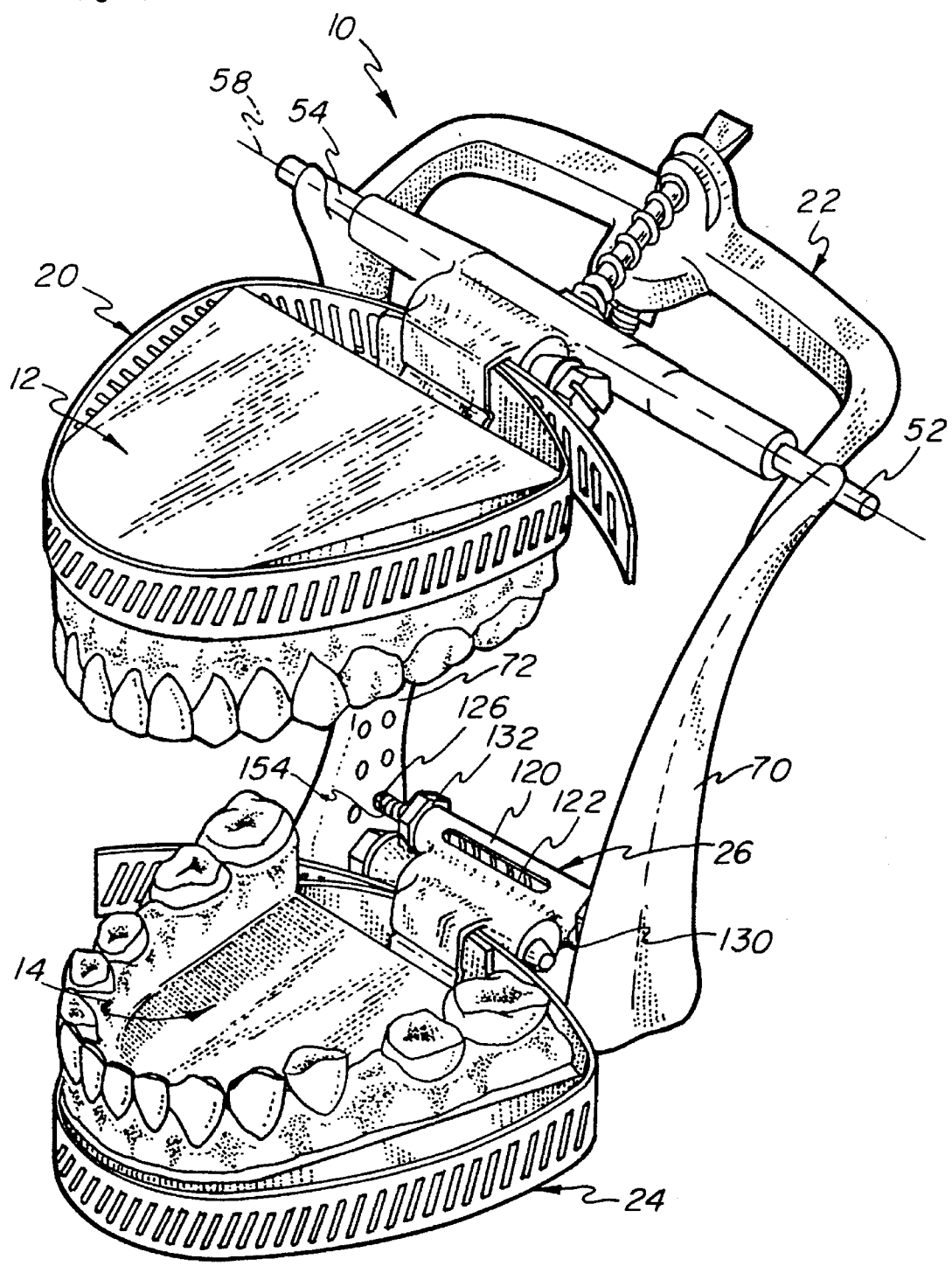
FIG. 1 is a perspective view showing a dental articulator according to the present invention mounting maxillary and mandibular dental castings.

FIG. 1 shows a dental articulator 10 according to the present invention mounting a maxillary model 12 and a mandibular model 14. The dental articulator 10 includes a maxillary clamp 20 mounting the maxillary model 12, a clamp support 22, a mandibular clamp 24 mounting the mandibular model 14, and a mandibular clamp detent 26.

As best shown in FIGS. 2 and 4, the maxillary clamp 20 includes a collet 30 formed from a flexible metal band defining periodic rectangular apertures 32 (FIG. 4) along substantially the entire length of the collet 30. A yoke 34 is coupled to a first portion 36 of the collet 30. The collet 30 is looped such that a second portion 38 (FIG. 2) of the collet 30 likewise enters the yoke 34. The yoke 34 positions a cam 40 such that a thread 42 defined by the cam 40 engages a portion (not shown) of the periodic rectangular apertures 32 defined in and around the second portion 38 of the collet 30. The cam 40 includes a head 44 having a slot 46 which may be engaged with a screwdriver (not shown) or similar hand tool to turn the cam 40 and tighten or loosen the collet 30.

The yoke 34 is coupled to a frame 50, preferably by welding, which is pivotally supported by the clamp support 22. As shown in FIGS. 2–4, the frame 50 is preferably a unitary casting which includes a pair of oppositely-projecting coaxial shafts 52, 54 and a tail 56 (FIG. 3). The shaft 52, 54 define a common axis 58 extending transversely with respect to the maxillary clamp 20. The tail 56 (FIG. 3) has a threaded bore 60 (FIG. 3) for engaging and supporting a threaded bolt or stop 62 (FIG. 3) and nut 64 (FIG. 3).

The clamp support 22 is preferably a unitary casting which includes a first post 70 and a second post 72 joined by a bracket 74. The first and second posts 70, 72 are formed as mirror-images of one another, and are shaped to approximate the contours of portions of a human mandible. The clamp support 22 also includes a pair of curved projections 76, 78 near the junctions between the first and second posts 70, 72 and the bracket 74. These curved fingers 76, 78 define journals 80, 82 for receiving and pivotally supporting the shafts 52, 54 of the frame 50.

The journals 80, 82 only partially surround the shafts 52, 54 so that the shafts may be slid into and out of the journals to install or remove the maxillary clamp 20 from engagement with the clamp support 22. The journals 80, 82 open toward the bracket 74, and the frame 50 is held in pivotal engagement with the clamp support 22 by a spring-mounted follower 84. The bracket 74 includes a boss 86 defining a smooth through bore 88 (FIG. 3). The follower 84 is slideably restrained in the bore 88 and a coiled spring 90 is trapped between the boss 86 and a head 92 on the follower 84 to bias the follower 84 toward the position of the frame 50. This structure permits the maxillary clamp 20 to be removed and another (not shown) to be substituted in its place if a dentist (not shown) must interrupt work on one set of dental models 12, 14 (FIG. 1) to work on another (not shown). Furthermore, the follower 84 acts as a stop to limit pivotal movement of the maxillary clamp 20 away from the mandibular clamp 24 by engaging either the yoke 34 or a welding bead (not shown) joining the frame 50 and the yoke.

Figure 5:
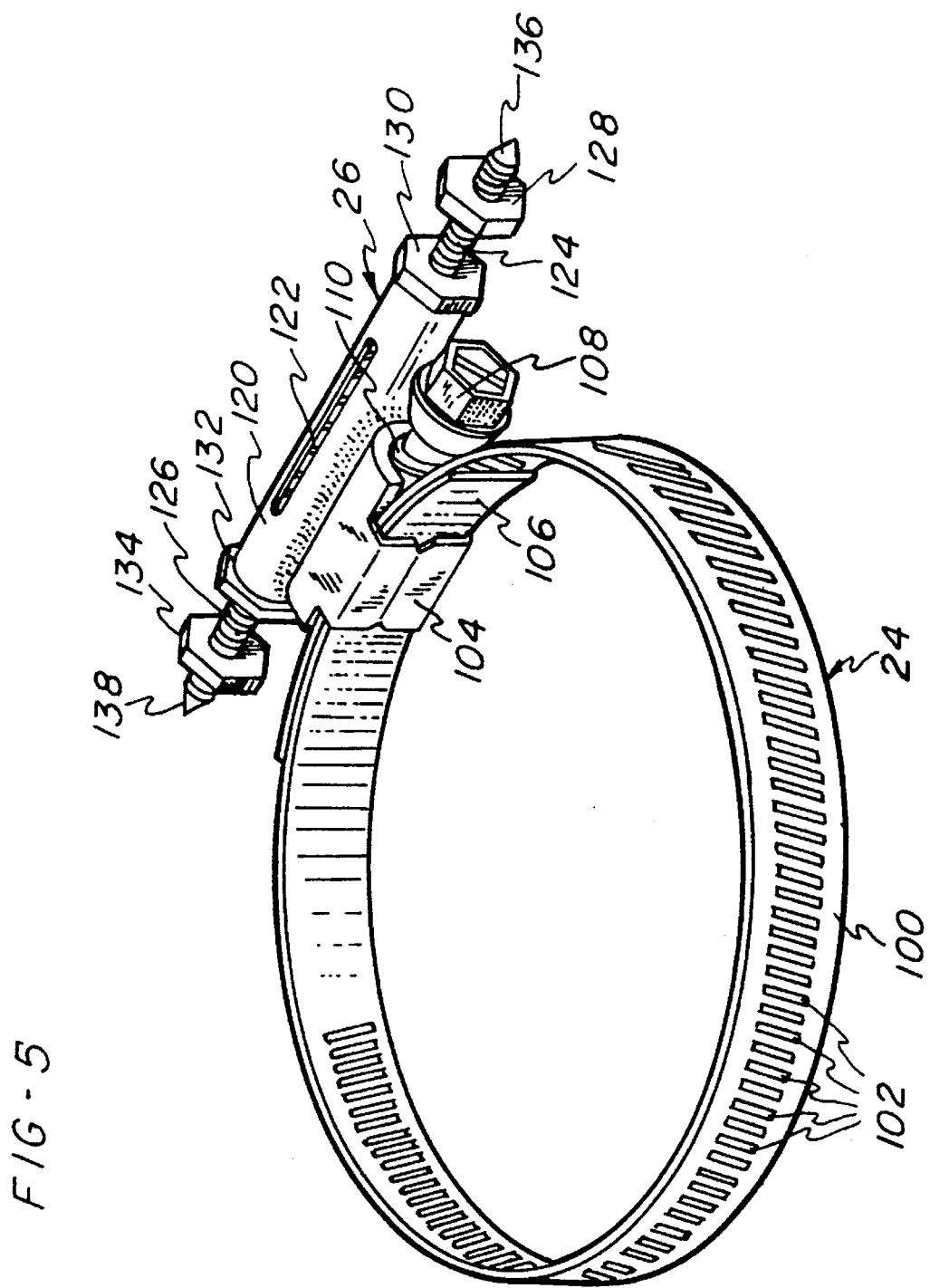
FIG. 5 is a perspective view of a mandibular clamp and a mandibular clamp detent for the dental articulator of FIG. 1.

As best shown in FIGS. 2, 4 and 5, the mandibular clamp 24 is similar in structure to the maxillary clamp 20, in that the mandibular clamp includes a collet 100 formed from a flexible metal band defining periodic rectangular apertures 102. A yoke 104 coupled to an end portion 106 of the collet 100 positions a cam 108 such that a thread 110 defined by the cam 108 engages a portion (not shown) of the periodic rectangular apertures 102 to tighten or loosen the collet 100.

The yoke 104 is coupled to a sleeve 120 of the mandibular clamp detent 26, preferably by welding. The sleeve 120 is preferably formed from a curled strip of a metal weldable to the yoke 104. As best shown in FIG. 5, the mandibular clamp detent 26 includes, apart from the sleeve 120, a coiled spring 122, a pair of oppositely-directed threaded pins 124, 126 and four nuts 128, 130, 132, 134. When assembled, the coiled spring 122 is housed in the sleeve 120. The two threaded pins 124, 126 each abut the coiled spring 122 at one end inside the sleeve 120. Pointed ends 136, 138 of the threaded pins 124, 126 project out of opposite ends of the sleeve 120. Two of the nuts, 128 and 130, engage the threaded pin 124 while the other two nuts, 132, and 134, engage the threaded pin 126.

As best shown in FIG. 3, the first and second posts 70, 72 define first and second sets of engagement sites 150, 152 for engagement with the mandibular clamp detent 26. The first and second sets of engagement sites 150, 152 each consist of 2–5 mm sockets 154, 156 defining engagement sites on opposed faces 158, 160 of the first and second posts 70, 72. Each socket 154' defining an engagement site on the first post 70 has a corresponding socket 156' defining an engagement site on the second post 72 such that an imaginary line 162 extending between the engagement site defined by the socket 154' and the corresponding engagement site defined by the socket 156' is parallel to the common axis 58 of the shafts 52, 54 when the shafts 52, 54 are engaged in the journals 80, 82, though other correspondences between the first and second sets of engagement sites 150, 152 are possible.

As best illustrated by reference to FIGS. 1 and 3, the mandibular clamp detent 26 is coupled to the clamp support 22 by squeezing the threaded pins 124, 126 into the sleeve 120 against the bias of the coiled spring 122; positioning the threaded pins 124, 126 such that their pointed ends 136, 138 are adjacent sockets 154', 156' (FIG. 3) defining corresponding engagement sites; and releasing the threaded pins 124, 126 such that their pointed ends 136, 138 (FIG. 6) engage the sockets 154', 156' (FIG. 3). The nuts 130, 132 are then turned on the threaded pins 124, 126 until the nuts 130, 132 abut the sleeve 120 to prevent the threaded pins 124, 126 from coming loose from engagement with the sockets 154', 156'. By pushing the sleeve 120 to one side or the other once the threaded pins 124, 126 have been engaged in the sockets 154', 156' and then tightening the nuts 130, 132 against the sleeve 120, the lateral relationship between the mandibular clamp 24 and the maxillary clamp 20 may be adjusted slightly to at least approximate lateral misalignment of the patient's teeth (not shown).

By selecting an appropriate pair sockets 154', 156' (FIG. 3), the mandibular clamp 24 is positioned relative to the maxillary clamp 20 such that the vertical bite and the protrusive misalignment of the patient's teeth are reproduced in the relative positions of the maxillary and mandibular models 12, 14. Preferably, the sets of engagement sites 150, 152 (FIG. 3) form two-dimensional arrays of engagement sites on the opposed faces 158, 160 of the first and second posts 70, 72 to permit the relative positions of the maxillary and mandibular clamps 20, 24 to be adjusted in two dimensions in an imaginary plane normal to the common axis 58 of the shafts 52, 54 so as to reproduce the vertical bite and protrusive misalignment of the patient's teeth.

The inclination of the mandibular clamp 24 (and, derivatively, of the mandibular model 14) is controlled by controlling the inclination of the mandibular clamp 24 when the threaded pins 124, 126 are engaged with the sockets 154', 156' The frictional engagement between the threaded pins 124, 126 and the sides of the sockets 154', 156' is sufficient to prevent pivotal movement of the mandibular clamp 24 relative to the clamp support 22. The inclination of the maxillary clamp 20 at the lower limit of its pivotal movement relative to the clamp support 22 is controlled by turning the stop 62 (FIG. 3) in the threaded bore 60 (FIG. 3) so that a head 170 of the stop 62 moves toward or away from the tail 56 (FIG. 3). The head 170 abuts against an abutment 172 on the bracket 74 of the clamp support 22, and the spacing between the tail 56 and the head 170 determines the inclination of the maxillary clamp 22 relative to the clamp support 22. The nut 64 may be adjusted on the stop 60 to fix its length relative to the tail 56.

Thus, for example, if a dentist (not shown) must interrupt work on one set of dental models 12, 14 to work on another (not shown), the dentist may quickly substitute the new set of dental models by turning the cams 34 and 104 to loosen the collets 30, 100 to release the dental models 12, 14; substitute the new dental models (not shown) for the dental models 12, 14 in the loosened collets 30, 100; and again turn the cams 34, 104 to tighten the collets 30, 100 to secure the new dental models. Alternatively, the dentist may remove the maxillary and mandibular clamps 20, 24 from the clamp support 22 without releasing the dental models 12, 14 and substitute new maxillary and mandibular clamps (not shown) holding the new dental models (not shown).

As discussed previously, the maxillary clamp 20 may be released from the clamp support 22 by manually drawing the follower 84 away from the frame 50 and sliding the shafts 52, 54 out of the journals 80, 82. The mandibular clamp 24 may be released from the clamp support 22 by manually squeezing the threaded pins 124, 126 out of engagement with the sockets 154', 156'. By recording the positions of the sockets 154', 156' as well as the inclination of the mandibular clamp 24 relative to the clamp support 22, and by maintaining the position of the stop 62, the models 12, 14 can be reinstalled after removal in the same relative positions and inclinations as they held prior to removal.

Various changes or modifications in the invention described may occur to those skilled in the art without departing from the true spirit or scope of the invention. The above description of preferred embodiments of the invention is intended to be illustrative and not limiting, and it is not intended that the invention be restricted thereto but that it be limited only by the true spirit and scope of the appended claims.

What is claimed is:

1. A dental articulator comprising:
   a maxillary clamp;
   a clamp support including a first post defining a first set of engagement sites, a second post defining a second set of engagement sites, and a hinge pivotally supporting the maxillary clamp;
   a mandibular clamp; and
   a mandibular clamp detent for engagement with corresponding engagement sites of the first and second sets of engagement sites to position the mandibular clamp relative to the maxillary clamp.

2. The dental articulator as recited in claim 1 wherein one of the maxillary and mandibular clamps includes a collet and a cam in threaded engagement with the collet for affecting the internal diameter of the collet.

3. The dental articulator as recited in claim 1 including a stop threadedly engaged with one of the maxillary clamp and the clamp support for abutment with the other of the maxillary clamp and the clamp support to control the inclination of the maxillary clamp relative to an axis of the hinge.

4. The dental articulator as recited in claim 1 wherein the first and second posts are shaped to approximate the contour of a portion of a human mandible.

5. The dental articulator as recited in claim 1 wherein the engagement sites of the first and second sets of engagement sites are defined by sockets in facing sides of the first and second posts.

6. The dental articulator as recited in claim 1 wherein the mandibular clamp detent is a spring-loaded detent.

7. The dental articulator as recited in claim 1 wherein the mandibular clamp detent includes a pair of oppositely-directed spring-loaded pins for engagement with corresponding engagement sites.

8. The dental articulator as recited in claim 1 wherein the mandibular clamp detent includes a sleeve coupled to the mandibular clamp, a spring positioned in the sleeve, a pair of threaded pins relatively biased by the spring and projecting out of the sleeve in different directions, and a pair of nuts each threadedly engaged with one of the pins for abutment against the sleeve to secure the mandibular clamp relative to the maxillary clamp.

9. A dental articulator comprising:
   a first collet for embracing a first dental model;
   a first cam threadedly engaging the first collet for tightening the first collet around such first dental model;
   a clamp support pivotally supporting the first collet;
   a second collet engaged with the clamp support for embracing a second dental model; and
   a second cam threadedly engaging the second collet for tightening the second collet around such second dental model.

10. The dental articulator as recited in claim 9 wherein one of the first and second collets includes a flexible band defining periodic apertures along a length of the band and wherein a corresponding one of the first and second cams defines a thread engaging a portion of the periodic apertures.

* * * * *